United States Patent [19]

Wahlig et al.

[11] Patent Number: 4,617,293

[45] Date of Patent: Oct. 14, 1986

[54] FLAVONOID PHOSPHATE SALTS OF AMINOGLYCOSIDE ANTIBIOTICS

[75] Inventors: Helmut Wahlig, Darmstadt; Elvira Dingeldein, Dreieich; Richard Kirchlechner, Rott a. Inn; Dieter Orth, Darmstadt; Werner Rogalski, Alsbach, all of Fed. Rep. of Germany

[73] Assignee: Merck Patent Gesellschaft mit beschraenkter Haftung, Darmstadt, Fed. Rep. of Germany

[21] Appl. No.: 613,131

[22] Filed: May 23, 1984

Related U.S. Application Data

[63] Continuation-in-part of Ser. No. 377,779, May 13, 1982, abandoned.

[30] Foreign Application Priority Data

May 13, 1981 [DE] Fed. Rep. of Germany ....... 3118856
Feb. 25, 1982 [DE] Fed. Rep. of Germany ....... 3206725

[51] Int. Cl.$^4$ ...................... A61K 31/71; C07H 15/22

[52] U.S. Cl. ........................................ 514/41; 514/37; 514/39; 536/8; 536/13.2; 536/13.3; 536/13.8; 536/14; 536/16.8

[58] Field of Search ................ 536/8, 13.2, 13.3, 13.8, 536/16.6, 14; 514/37, 41, 39

[56] References Cited

U.S. PATENT DOCUMENTS 2,962,495 11/1960 Ferno et al. ............................ 536/8
3,091,572 5/1963 Luedemann et al. ............... 536/13.6

OTHER PUBLICATIONS

Rinehart, Jr. and Suami, Ed., Aminocyclitol Antibiotics, ACS Symposium Series 125, Washington, D.C., 1980.

Primary Examiner—Johnnie R. Brown
Assistant Examiner—Elli Peselev
Attorney, Agent, or Firm—Millen & White

[57] ABSTRACT

Flavonoid phosphates of aminoglycoside antibiotics are useful sparingly soluble salts, e.g., for achieving a depot effect.

12 Claims, No Drawings

4,617,293

FLAVONOID PHOSPHATE SALTS OF AMINOGLYCOSIDE ANTIBIOTICS

This application is a continuation-in-part of U.S. Ser. No. 377,779, filed on May 13, 1982, now abandoned, May 24, 1984 and whose disclosure is incorporated by reference herein.

BACKGROUND OF THE INVENTION

The present invention relates to new sparingly soluble salts of aminoglycoside antibiotics.

Aminoglycoside antibiotics such as gentamycin or tobramycin are usually employed in the form of their sulfates, which are readily soluble in water. The antibiotics are rapidly released from these salts and distribute themselves around the body. In some cases, this property is a disadvantage, in particular if a locally limited infection is to be combatted, for example an infected bone. In these cases, more sparingly soluble salts, from which the antibiotic is released more slowly and which therefore can display a certain depot action, are desirable.

Some sparingly soluble salts of aminoglycoside antibiotics are known. Thus, for example, U.S. Pat. No. 3,091,572 mentions various sparingly soluble salts of gentamycin (for example, salts of fatty acids containing 8 or more C atoms, e.g., lauric acid, stearic acid, palmitic acid or oleic acid; aralkanoic acids, e.g., phenylbutyric acid; arylcarboxylic acids, e.g., naphthalene-1-carboxylic acid; and sulfuric and sulfonic acids, e.g., laurylsulfuric acid and dodecylbenzenesulfonic acid).

It has been found that these salts display certain disadvantages when used For example, they have a waxy, clearly hydrophobic nature which impedes their galenical processing.

SUMMARY OF THE INVENTION

Accordingly, it is an object of this invention to provide new salts of antibiotics which are sparingly soluble and which do not have the adverse properties of the known antibiotic salts or display them only to a minor degree.

Upon further study of the specification and appended claims, further objects and advantages of this invention will become apparent to those skilled in the art.

These objects have been achieved by this invention and the finding that a slower release of the antibiotics can be achieved if the sparingly soluble flavonoid phosphates, in particular the hesperidin-phosphates, of the aminoglycoside antibiotics are used instead of the mentioned sulfates or other readily soluble salts.

This invention accordingly relates to the flavonoid phosphates, in particular the hesperidin-phosphates, of aminoglycoside antibiotics.

DETAILED DISCUSSION

Suitable anionic components of the salts of this invention include phosphoric acid half-esters of hydroxy-flavonoids, for example of hydroxy-flavanes, -flavenes, -flavanones, -flavones or -flavylium salts. The flavanone and flavone derivatives are preferred.

The hydroxyflavonoids can contain one or more, for example 1, 2, 3, 4, 5, 6 or 7, preferably 1, 2, 3 or 4, hydroxy groups, which are preferably of a phenolic nature, but can also be of the alcoholic type. They are as a rule in the 3-, 5-, 6-, 7-, 3'- and/or 4'-position of the flavane system, but can also be in the 4-, 8-, 2'-, 5'- or 6'-position. The 3'- and 5-positions are preferred.

One or more of the hydroxy groups can be esterified with phosphoric acid. This, for example, the 3'- and 5-monophosphates and the 3',5-diphosphate of hesperidin can be used as salt-forming component. In all of the following text, the expression "hesperidin-phosphoric acid" relates to the 3',5-diphosphate and the expression "hesperidin-phosphate(s)" relates to the salts derived therefrom.

In addition to the phosphorylated and free OH groups, the flavonoid phosphoric acids can also carry other substituents, for example etherified OH groups, such as alkoxy groups of, preferably, 1–4 C atoms, above all methoxy groups (as a rule not more than three, preferably one, and preferably in the 4'-position, but also in the 3-, 3'-, 5-, 6- and/or 7-position), and, in particular, glycosidated OH groups. These can be glycosidated with mono-, di-, tri- or tetra-saccharides. Preferred glycoside components are monosaccharides, e.g., D-glucose, and also D-galactose, D-glucuronic acid, D-galacturonic acid, D-xylose, D-apiose, L-rhamnose and L-arabinose, and disaccharides, e.g., rhamnosylglucoses, particularly preferably rutinose and neohesperidose, and also, for example, rungiose, robinobiose, sophorose, gentiobiose, apiobiose, vicianose, sambubiose, primverose or latyrose. Glycosidated OH groups are preferably in the 7- and/or 3-position; at most 2, and preferably one, glycosidated OH group is as a rule present in the molecule of the flavonoid phosphoric acid. Examples of other possible substituents (as a rule not more than 3, preferably only one) include alkyl of, for example, 1–4 C atoms, preferably methyl, halogen, preferably F or Cl, and hydroxyalkoxy of, for example, 1–4 C atoms, preferably 2-hydroxyethoxy.

Examples of specific flavonoid phosphates include phosphoric acid half-esters of hydroxyflavanes, e.g., 6-hydroxy-4'-methoxyflavane, 6-hydroxy-3,4'-dimethoxyflavane, 6-hydroxy-4'-methoxy-3-methylflavane, catechol ((+)-3,3',4',5,7-pentahydroxyflavane) and leucocianidol (3,3',4,4',5,7-hexahydroxyflavane) and glycosides thereof, e.g., 2,3,3',4,4',5,7-heptahydroxyflavane glucoside; hydroxyflavanones, e.g., liquiritigenin (4',7-dihydroxyflavanone), pinocembrin (dihydrochrysin, 5,7-dihydroxyflavanone), naringenin (4',5,7-trihydroxyflavanone), eriodictyol (3',4',5,7-tetrahydroxyflavanone), dihydroquercetin (taxifolin, 3,3',4',5,7-pentahydroxyflavanone), 6-hydroxy-4'-methoxyflavanone, sacuranetin (4',5-dihydroxy-7-methoxy-flavanone), isosacuranetin (5,7-dihydroxy-4'-methoxy-flavanone), hesperetin (3',5,7-trihydroxy-4'-methoxyflavanone) and silibinin (2-[trans-2-(4-hydroxy-3-methoxyphenyl)-3-hydroxymethyl-1,4-benzodioxan-6-yl]-3,5,7-trihydroxychroman-4-one) and glycosides thereof, e.g., pinocembrin 7-rutinoside, sarothanoside (pinocembrin 7-neohesperidoside), salipurposide (naringenin 5glucoside), prunin (naringenin 7-glucoside), narirutin (naringenin 7-rutinoside), naringin (naringenin 7-neohesperiodoside), eriodictin (eriodictyol 7-rhamnoside), eriocitrin (eriodictyol 7-rutinoside), eriodictyol 7-neohesperidoside, didymin (isosacuranetin 7-rutinoside), poncirin (isosacuranetin 7-neohesperidoside), persicoside (hesperitin glucoside), hesperidin (hesperetin 7-rutinoside), and neohesperidin (hesperetin 7-neohesperidoside); hydroxyflavones, e.g., chrysin (5,7-dihydroxyflavone), primetin (5,8-dihydroxyflavone), galangin (3,5,7-trihydroxyflavone), baicalein (5,6,7-trihydroxyflavone), apigenin (4',5,7-trihydroxyflavone), datiscetin (2',3,5,7- tetrahydroxyflavone), lotoflavin (2',4',5,7-tetrahydroxyflavone), caempferol (3,4',5,7-tetrahydroxyflavone), fisetin (3,3',4',7-tetrahydroxyflavone), luteolin (3',4',5,7-tetrahydroxyflavone), scutellarein (4',5,6,7tetrahydroxyflavone), morin (2',4,4',5,7-pentahydroxyflavone), robinetin (3,3',4'5',7-pentahydroxyflavone), quercetin (3,3',4',5,7-pentahydroxyflavone), tectochrysin (5-hydroxy-7-methoxyflavone), genkwanin (4',5-dihydroxy-7-methoxyflavone), acacetin (5,7-dihydroxy-4'-methoxyflavone), diosmetin (3',5,7-trihydroxy-4'-methoxyflavone), chrysoeriol (4',5,7-trihydroxy-3'-methoxyflavone), rhamnetin (3,3',4',5-tetrahydroxy-7-methoxyflavone), isorhamnetin (3,4',5,7-tetrahydroxy-3'-methoxyflavone), chloroflavonin (3'-chloro-2',5-dihydroxy-3,7,8-trimethoxyflavone) and eupatorin (3',5-dihydroxy-4',6,7-trimethoxyflavone) and glycosides thereof, e.g., chrysin 7-rutinoside, chrysin 7-neohesperidoside, apiin (apigenin 7-apiosylglucoside), rhoifolin (apigenin 7-neohesperidoside), isorhoifolin (apigenin 7-rutinoside), nicotiflorin (caempferol 3-rutinoside), lespedin (caempferol 3,7-dirhamnoside), robinin (caempferol 3-robinoside 7-rhamnoside), scolymoside (lonicerin, luteolin 7-rutinoside), veronicastroside (luteolin 7-neohesperidoside), quercitrin (quercetin 3-rhamnoside), isoquercitrin (quercetin 3-glucoside), hyperoside (quercetin 3-galactoside), rutoside (rutin, quercetin 3-rutinoside), 6-hydroxymethylrutoside, monoxerutin [7-(2-hydroxyethyl)-rutoside], ethoxazorutoside [4'-O-(2-morpholinoethyl)-rutoside], troxerutin [3',4',7-tris-(2-hydroxyethyl)-rutoside], acaciin (linarin, acacetin 7-rutinoside), fortunellin (acacetin 7-neohesperidoside), diosmin (diosmetin 7-rutinoside), neodiosmin (diosmetin 7-neohesperidoside) and narcissin (isorhamnetin 3-rutinoside); hydroxyflavylium salts, e.g., cyanidin and glycosides thereof, e.g., keracyanin (cyanidin 3-rutinoside).

Suitable aminoglycoside antibiotics include, in particular, those which contain a deoxystreptamine unit. Specific examples which are particularly preferred are amikacin, dibekacin, gentamycin, the neomycins, paromomycin, sagamycin, sisomicin, streptomycin and tobramycin, and further preferred examples are allomycin, amicetin, apramycin, bekanamycin, betamicin, butirosin, destomycin, the everninomycins, the ezomycins, flambamycin, fortimycin A and B, framycetin, hikizimycin, homomycin, hybrimycin, hygromycin, the kanamycins, kasugamycin, lividomycin, minosaminomycin, the myomycins, netilmicin, parvulomycin, puromycin A, ribostamycin, rimocidin, ristomycin, ristosamine, the seldomycins, sorbistin, spectinomycin, streptothricin, tunicamycin and verdamycin and epimers and derivatives thereof which are basic. The meaning of "aminoglycoside antibiotics" (or "aminocyclitol antibiotics") is well-known to those in the field and is described, e.g., in "Aminocyclitol Antibiotics" (Ed.: K. L. Rinehart, Jr., and T. Suami; ACS Symposium Series, Washington, D.C., 1980), whose disclosure is incorporated by reference herein.

Since some of these antibiotics, for example gentamycin, are known not to be single substances but mixtures (gentamycin is, for example, a mixture of the compounds gentamycin C 1, gentamycin C 2 and gentamycin C 1a), the flavonoid phosphates in some cases are correspondingly also not single substances but mixtures. Moreover, since many of the antibiotics mentioned, for example all the gentamycins, contain several basic nitrogen atoms, and since, on the other hand, flavonoid phosphoric acids such as hesperidinphosphoric acid are polybasic acids, it is furthermore possible for acid, neutral and/or basic salts to be formed. All these possible salts and their mixtures with one another are included in the term "a flavonoid phosphate of an aminoglycoside antibiotic" and analogous terms used herein.

The neutral salts and mixtures containing these are preferred. In the case of the gentamycin hesperidin-phosphates, for example, the salt (mixture) of 2 moles of gentamycin and 5 moles of hesperidin-phosphoric acid is particularly preferred. ("Neutral" in this context means that there is one basic amino group per phosphoric acid radical).

The invention also relates to a process for the preparation of flavonoid phosphates of aminoglycoside antibiotics, comprising reacting a water-soluble salt of an aminoglycoside antibiotic with a flavonoid phosphate or one of its water-soluble salts.

The preparation is carried out in a manner which is known per se, for example by bringing together an aqueous solution of the water-soluble salt of the antibiotic (for example gentamycin sulfate) and an aqueous solution of the flavonoid phosphate or one of its water-soluble salts (for example the disodium salt), preferably while stirring and at room temperature. An organic solvent, for example an alcohol, such as ethanol, may also be added to improve the solubility. The flavonoid phosphates formed are sparingly soluble in water and can be obtained by filtering, washing with water, and drying.

This invention furthermore relates to the use of the flavonoid phosphates for the preparation of pharmaceutical formulations, in particular by a non-chemical route. For this, they can be brought into a suitable dosage form together with at least one solid, liquid or semi-liquid excipient or auxiliary, if appropriate in combination with one or more other active compound(s).

The invention furthermore relates to agents, in particular pharmaceutical formulations, containing at least one flavonoid phosphate of an aminoglycoside antibiotic of this invention.

These formulations can be used as medicaments in human or veterinary medicine for administration, e.g., to mammals including humans. Suitable excipients are organic or inorganic substances which are suitable for enteral (for example oral) or parenteral administration or topical application and which do not react with the new compounds, for example water, vegetable oils, benzyl alcohols, polyethylene glycols, glycerol triacetate, gelatin, carbohydrates, such as lactose or starch, magnesium stearate, talc or petroleum jelly. Tablets, dragees, capsules, syrups, elixirs or drops are used, in particular, for oral administration, suppositories are used for rectal administration, solutions, suspensions, emulsions or implants are used for parenteral administration, and ointments, creams or powders are used for topical application. Implants containing the new salts, e.g., based on silicone rubber, tricalcium phosphate or collagen, which are suitable, for example, for the treatment of infected bone, are of particular importance. The new compounds can also be lyophilized and the resulting lyophilizates can be used, for example, for the preparation of injection products. The formulations mentioned can be sterilized and/or can contain auxiliaries, such as lubricants, preservatives, stabilizers and/or wetting agents, emulsifiers, salts for influencing the osmotic pressure, buffer substances, colorants, flavor substances and/or aroma generating substances. If desired, they can also contain one or more other active compounds, for example readily soluble salts of the same or different antibiotics, in order to achieve a systemic action in addition to the depot effect caused by the flavonoid phosphates. In general, the administration and use of the novel salts of this invention is fully conventional and analogous to the prior art use of known antibiotic preparations.

This invention particularly relates to a new fibrin/antibiotic gel which contains at least one flavonoid phosphate of an aminoglycoside antibiotic of this invention.

Fibrin/antibiotic gels which contain tobramycin, gentamycin and/or one of their physiologically acceptable salts as the antibiotic are known from International Patent Application No. WO 81/00516, corresponding to U.S. application Ser. No. 261,223, filed on Apr. 27, 1981, whose disclosures are entirely incorporated by reference herein. Therein, only the sulfates are mentioned specifically as physiologically acceptable salts of the two antibiotics. However, these known fibrin/antibiotic gels which contain tobramycin sulfate or gentamycin sulfate have the disadvantage when used in practice, for example in the treatment of infected bone, that the antibiotics are released from them too rapidly. The antibiotics distribute themselves about the body and are partly excreted; they can then no longer be effective to the desired extent at the actual infection site. The new fibrin/antibiotic gel does not have these adverse properties of the known gels, or has them only to a minor degree.

The gentamycin salts can be used in the form in which they are obtained or in finely divided, for example, micronized, form for the preparation of the fibrin-/antibiotic gels.

The fibrin/antibiotic gels can be prepared in a manner which is known per se, preferably by mixing a fibrinogen solution, a thrombin solution and the new flavonoid phosphate of an aminoglycoside antibiotic. The fibrin is thereby precipitated. The thrombin solution preferably additionally contains aprotinin and/or is enriched with calcium ions, for example in the form of $CaCl_2$. Apart from the flavonoid phosphates, all the constituents of the gel are advantageously used in the form of conventional commercially available products. It is possible to form the gel first at the chosen location, for example directly in the bone cavity, by addition of the thrombin solution to the fibrinogen solution, the salt of the antibiotic being added beforehand either to the thrombin solution or to the fibrinogen solution. However, the gel is preferably prepared by mixing the constituents outside the body. In both cases, the coagulation operation of the fibrin can be controlled with respect to time by changing the concentration of the thrombin.

The fibrinogen can be used, for example, in the form of human fibrinogen as a commercially available cryoprecipitate which contains about 90 mg/ml of protein which can be precipitated with thrombin, or in the form of a lyophilizate, for example obtained from human blood from pooled donor plasma. The fibrin/antibiotic gel preferably contains about 2 to about 10, preferably about 3 to 6, percent by weight of fibrin.

The thrombin solution is preferably prepared by dissolving thrombin (for example in the form of a powder) in an aqueous calcium chloride solution. This can contain, for example, 1,000 to 10,000 KIU (kallikrein inactivator units), preferably about 3,000 KIU, of aprotinin per ml. The concentration of calcium chloride is preferably about 20 to 60, in particular about 40, mmols/l. The concentration of the thrombin is preferably about 10 to about 500 NIH units per ml. About the same volumes of fibrinogen solution and thrombin solution are preferably used for preparing the gel.

The salt of the antibiotic is advantageously used in an amount based on the body weight, and the maximum daily dose should be taken into consideration. The concentration of the antibiotic in the fibrin/antibiotic gel is preferably between about 0.5 and about 10, in particular between 1 and 5, percent by weight, relative to the base of the aminoglycoside antibiotic.

The coagulation time of the gel depends on the thrombin concentration. The plastic formability of the resulting coagulant can be maintained for a period of ½ to 1 minute if a thrombin concentration of about 150 NIH units per ml is used. The flow properties of the gel are maintained for a considerably longer period (for example up to 3 minutes) by a lower thrombin concentration (10–15 NIH units/ml). The coagulation of the fibrin is thereby slowed down, and the tensile strength of the polymer is rather increased.

As well as the salts which can be used according to the invention, the gels can additionally also contain other physiologically acceptable gentamycin salts, for example the sulfate or gentamycin base, as well as other antibiotics, such as tobramycin, neomycin, streptomycin, penicillins, bacitracin, clindamycin and/or physiologically acceptable salts thereof. The gels can also contain other active compounds.

In cases of primary spongiosa graft, the fibrin/antibiotic gel not only controls infection but also improves the osteogenetic potency of the biological implant.

Bone which is in danger of infection, for example following open fractures, can, of course, also be treated with the fibrin/antibiotic gel to prevent infection. In this case, a particularly high local level of active compound is achieved by the special gentamycin or other salts of this invention.

The delayed release of the antibiotic from the fibrin-/antibiotic gels according to the invention in comparison with the release from gels obtained with gentamycin sulfate or other conventional antibiotics can be demonstrated in a manner which is known per se, the antibiotic released preferably being determined microbiologically. This determination can be effected in vitro, for example by elution in aqueous buffer solution or animal or human serum. The rate of excretion in the urine or the change of the concentration in the serum or in tissues with respect to time can also be determined in the same way following implantation of the gel in vivo or following a bone operation. In vivo experiments can be carried out on any desired experimental animals, for example rats, rabbits or dogs, or on humans.

The invention also relates to the use of the flavonoid phosphates mentioned in combating illnesses, in particular bacterial infections, and to their use in the therapeutic treatment of the human or animal body.

The substances of this invention are preferably administered for these purposes in dosages of about 5 to 1,000 mg, in particular 10 to 500 mg, per dosage unit (relative to the antibiotically active compound). The particular dose for each particular patient depends, however, on the most diverse conventional factors, for example, on the effectiveness of the particular compound employed; the age, weight, general state of health, sex, and diet of the patient; the time and route of administration; the excretion rate; the medicament combination; and the severity of the particular illness to which the therapy applies. Local administration is preferred.

The new flavonoid phosphates are effective against microorganisms, particularly against gram positive, gram negative and acid fast bacteria. They can be used to combat the same kinds of bacteria which can be combatted by means of the aminoglycoside antibiotics themselves. Typical bacteria for which the flavonoid phosphates are effective against include *Staphylococcus aureus, Streptococcus fecalis, Bacillus subtilis, Escherichia coli, Salmonella schottmuelleri, Pseudomonas aeruginosa, Klebsiella pneumoniae, Mycobacterium smegmatis, Mycobacterium tuberculosis.*

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A solution of 20.4 g (25 mmols) of disodium hesperidin-5,3'-diphosphate in 600 ml of water is added to a solution of 7.07 g (10 mmols) of gentamycin sulfate in 200 ml of water at 20°, while stirring.

Stirring is continued for one hour; the resulting gentamycin hesperidin-phosphate (gentamycin . 2.5 hesperidin-phosphate) is filtered off with suction, rinsed with water and dried over KOH. M.p. 227°–229° (decomposition); IR spectrum (in KBr): 3410, 2950, 1637, 1572, 1510 and 1440 cm$^{-1}$.

EXAMPLES 2 to 8

The following compounds are obtained from the stoichiometrically calculated amounts of the sulfates of the corresponding antibiotics and disodium hesperidin-5,3'-diphosphate analogously to Example 1:

2. Neomycin hesperidin-phosphate (=neomycin . 3 hesperidin-phosphate), m.p. 228°–230° (decomposition).
3. Paromomycin hesperidin-phosphate (=paromomycin . 2.5 hesperidin-phosphate), m.p. 219°–222° (decomposition).
4. Sisomycin hesperidin-phosphate (=sisomycin . 2.5 hesperidin-phosphate), m.p. 220°–221° (decomposition).
5. Amikacin hesperidin-phosphate (=amikacin . 2 hesperidin-phosphate), m.p. 226°–229° (decomposition).
6. Tobramycin hesperidin-phosphate (=tobramycin . 2.5 hesperidin-phosphate), m.p. 228° (decomposition).
7. Dibekacin hesperidin-phosphate (=dibekacin . 2.5 hesperidin-phosphate), m.p. 230° (decomposition).
8. Streptomycin hesperidin-phosphate (=streptomycin . 3 hesperidin-phosphate), m.p. 212°–213° (decomposition).

EXAMPLE 9

A solution of 7.07 g of gentamycin sulfate in 200 ml of water is added to a solution of 17.5 g (50 mmols) of 6-hydroxy-4'-methoxy-flavanone-6-phosphoric acid ester in 150 ml of ethanol and 1,600 ml of water at 20°, while stirring. Stirring is continued for one hour and the resulting gentamycin salt of 6-hydroxy-4'-methoxy-flavanone-6-phosphoric acid ester is filtered off with suction, rinsed with water and dried over KOH. M.p. 210°–215° (sintering at 190°).

The examples which follow relate to pharmaceutical formulations which contain hesperidin-phosphates of aminoglycoside antibiotics:

EXAMPLE A

Capsules 10 kg of neomycin hesperidin-phosphate is introduced into hard gelatin capsules in conventional fashion, so that each capsule contains active compound corresponding to 165 mg of neomycin base.

EXAMPLE B

Ampoules 1 kg of gentamycin hesperidin-phosphate is finely micronized and suspended in 30 l of sesame oil and the suspension is introduced into ampoules, which are sealed under sterile conditions. Each ampoule contains active compound corresponding to 10 (40, 80, 120) mg of gentamycin base.

EXAMPLE C

Implants 1.54 g of micronized gentamycin hesperidin-phosphate (corresponding to 0.2 g of gentamycin) is mixed with 8.5 g of silicone rubber monomer (Medical Grade Silastic 382, Dow Corning); 2 drops of polymerization catalyst are added; the components are mixed again; and the mixture is shaped into circular discs 20 mm in diameter and 1 mm thick. Each disc contains 6 mg of gentamycin base.

EXAMPLE D

Fibrin/antibiotic gel

4 NIH units of thrombin (commercial product) is dissolved in 1 ml of aprotinin/calcium chloride solution (commercial product; 3,000 KIU/ml of aprotinin in 40 mmols/l of CaCl$_2$); the solution is warmed to 37°; an amount of gentamycin hesperidin-phosphate corresponding to 20 mg of gentamycin base is added; and the mixture is mixed with the same amount of "fibrin adhesive" (commercial product; prepared by low-temperature precipitation from human donor plasma; stored at −18° or below; 1 ml of the solution contains on average 90 mg of protein which can be precipitated with thrombin, total protein content of the solution about 10 percent by weight; thawed for about 20–30 minutes before the planned use), which has been prewarmed to 37°. The mixture is allowed to solidify in stainless steel cylinders {internal diameter 6 mm, height 10 mm) (1 ml for 3 cylinders). The gel cylinders formed are then ejected from the molds.

The new compounds mentioned in Examples 1 to 9 as well as the pharmaceutical formulations containing them have excellent antibiotic activity.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A flavonoid phosphate of an aminoglycoside antibiotic, or a mixture thereof.

2. A compound or mixture of claim 1, wherein the flavonoid phosphate is a phosphoric acid half-ester of an hydroxy-flavane, -flavene, -flavanone, -flavone or -flavylium salt.

3. A compound or mixture of claim 1 or 2, wherein the aminoglycoside antibiotic contains a deoxystreptamine unit.

4. A compound or mixture of claim 1, wherein the flavonoid phosphate is an hesperidin phosphate.

5. A compound or mixture of claim 1, wherein the flavonoid phosphate is gentamycin hesperidin-phosphate.

6. Compounds or mixtures of claim 1 selected from the group consisting of neomycin hesperidin-phosphate; paromomycin hesperidin-phosphate; sisomycin hesperidin-phosphate; amikacin hesperidin-phosphate; tobramycin hesperidin-phosphate; dibekacin hesperidin-phosphate; or streptomycin hesperidin-phosphate.

7. A compound of claim 1 wherein the flavanoid phosphate is a phosphoric acid half-ester of 6-hydroxy-4'-methoxyflavane, 6-hydroxy-3,4'-dimethoxyflavane, 6-hydroxy-4'-methoxy-3-methylflavane, catechol ((+)-3,3',4',5 7-pentahydroxyflavane), leucocianidol (3,3',4,4',5,7-hexahydroxyflavant), 2,3,3',4,4',5,7-heptahydroxyflavane glucoside, liquiritigenin (4',7-dihydroxyflavanone), pinocembrin (dihydrochrysin, 5,7-dihydroxyflavanone), naringenin (4',5,7-trihydroxyflavanone), eriodictyol (3',4',5,7-tetrahydroxyflavanone), dihydroquercetin (taxifolin, 3,3',4',5,7-pentahydroxyflavanone), 6-hydroxy-4'-methoxyflavanone, sacuranetin (4',5-dihydroxy-7-methoxy-flavanone), isosacuranetin (5,7-dihydroxy-4'-methoxy-flavanone), hesperetin (3',5,7-trihydroxy-4'-methoxy-flavanone), silibinin (2-[trans-2-(4-hydroxy-3-methoxyphenyl)-3-hydroxymethyl-1,4-benzodioxan-6-yl-]-3,5,7-trihydroxychroman-4-one), pinocembrin 7-rutinoside, sarothanoside (pinocembrin 7-neohesperidoside), salipurposide (naringenin 5-glucoside), prunin (naringenin 7-glucoside), narirutin (naringenin 7-rutinoside), naringin (naringenin 7-neohesperiodoside), eriodictin (eriodictyol 7-rhamnoside), eriocitrin (eriodictyol 7-rutinoside), eriodictyol 7-neohesperidoside, didymin (isocacuranetin 7-rutinoside), poncirin (isosacuranetin 7-neohesperidoside), persicoside (hesperitin glucoside), hesperidin (hesperetin 7-rutinoside), neohesperidin (hesperetin 7-neohesperidoside), chrysin (5,7-dihydroxyflavone), primetin (5,8-dihydroxyflavone), galangin (3,5,7-trihydroxyflavone), baicalein (5,6,7-trihydroxyflavone), apigenin (4'5,7-trihydroxyflavone), datiscetin (2',3,5,7-tetrahydroxyflavone), lotoflavin (2',4',5,7-tetrahydroxyflavone), caempferol (3,4',5,7-tetrahydroxyflavone), fisetin (3,3',4',7-tetrahydroxyflavone), luteolin (3',4',5,7-teatrahydroxyflavone), scutellarein (4',5,6,7-tetrahydroxyflavone), morin (2',4,4',5,7-pentahydroxyflavone), robinetin (3,3',4',5',7-pentahydroxyflavone), quercetin (3,3',4',5,7-pentahydroxyflavone), tectochrysin (5-hydroxy-7-methoxyflavone), genkwanin (4',5-dihydroxy-7-methoxyflavone), acacetin (5,7-dihydroxy-4'-methoxyflavone), diosmetin (3',5,7-trihydroxy-4'-methoxyflavone), chrysoeriol (4',5,7-trihydroxy-3'-methoxyflavone), rhamnetin (3,3',4',5-tetrahydroxy-7-methoxyflavone), isorhamnetin (3,4',5,7-tetrahydroxy-3'-methoxyflavone), chloroflavonin (3'-chloro-2',5-dihydroxy-3,7,8-trimethoxyflavone), eupatorin (3',5-dihydroxy-4',6,7-trimethoxyflavone), chrysin 7-rutinoside, chrysin 7-neohesperidoside, apiin (apigenin 7-apiosylglycoside), rhoifolin (apigenin 7-neohesperidoside), isorhoifolin (apigenin 7-rutinoside), nicotiflorin (caemferol 3-rutinoside), lespedin (caempferol 3,7-dirhamnoside), robinin (caempferol 3-robinoside 7-rhamnoside), scolymoside (lonicerin, luteolin 7-rutinoside), veronicastroside (luteolin 7-neohesperidoside), quercitrin (quercetin 3-rhamnoside), isoquercitrin (quercetin 3-glucoside), hyperoside (quercetin 3-galactoside), rutoside (rutin, quercetin 3-rutinoside), 6-hydroxymethylrutoside, monoxerutin [7-(2-hydroxyethyl)-rutoside], ethoxazorutoside [4'-O-(2-morpholinoethyl)-rutoside], troxerutin [3',4',7-tris-(2-hydroxyethyl)-rutoside], acaciin (linarin, acacetin 7-rutinoside), fortunellin (acacetin 7-neohesperidoside), diosmin (diosmetin 7-rutinoside), neodiosmin (diosmetin 7-neohesperidoside), narcissin (isorhamnetin 3-rutinoside) or keracyanin (cyanidin 3-rutinoside).

8. A compound of claim 1 wherein the aminoglycoside antibiotic is amikacin, dibekacin, gentamycin, a neomycin, paromomycin, sagamycin, sisomicin, streptomycin, tobramycin, allomycin, amicetin, apramycin, bekanamycin, betamicin, butirosin, destomycin, an everninomycin, fortimycin A or B, framycetin, homomycin, hybrimycin, hygromycin, a kanamycin, kasugamycin, lividomycin, minosaminomycin, a myomycin, netilmicin, puromycin A, ribostamycin, rimocidin, ristomycin, ristosamine, a seldomycin, sorbistin, spectinomycin, streptothricin, tunicamycin or verdamycin.

9. A pharamaceutical composition comprising an antibiotically effective amount of a compound of claim 1 and a pharmaceutically acceptable carrier.

10. In a pharmaceutical composition which is a fibrin antibiotic gel, the improvement wherein the antibiotic is a flavonoid phosphate of an aminoglycoside antibiotic, or a mixture thereof of according to claim 1.

11. A method of achieving an antibiotic effect in a patient comprising administering an antibiotically effective amount of a compound of claim 1 to the patient.

12. A method of claim 11, wherein the patient is treated with said compound for the purpose of treating a bone defect.

* * * * *